United States Patent [19]

Nishihira et al.

[11] Patent Number: 5,463,109
[45] Date of Patent: Oct. 31, 1995

[54] PROCESS FOR PREPARING CARBAMATES

[75] Inventors: Keigo Nishihira; Shuji Tanaka, both of Ube, Japan

[73] Assignee: Ube Industries, Ltd., Yamaguchi, Japan

[21] Appl. No.: 379,118

[22] Filed: Jan. 27, 1995

Related U.S. Application Data

[63] Continuation of Ser. No. 976,669, Nov. 16, 1992, abandoned, which is a continuation of Ser. No. 673,403, Mar. 22, 1991, abandoned.

[30] Foreign Application Priority Data

Mar. 27, 1990 [JP] Japan .................................... 2-75661

[51] Int. Cl.$^6$ .................... C07C 269/00; C07C 269/04
[52] U.S. Cl. .................... 560/157; 560/24; 560/115; 560/162; 560/163
[58] Field of Search .................... 560/24, 115, 157, 560/162, 163

[56] References Cited

U.S. PATENT DOCUMENTS

| | | | |
|---|---|---|---|
| 3,013,064 | 12/1961 | Beinfest et al. | 260/482 |
| 4,268,684 | 5/1981 | Gurgiolo | 560/25 |
| 4,484,994 | 11/1984 | Jacobs, II et al. | 204/181 C |
| 4,520,167 | 5/1985 | Blank et al. | 525/131 |
| 4,725,680 | 2/1988 | Barcelo et al. | 560/157 |
| 4,897,435 | 1/1990 | Jacobs, III et al. | 523/414 |
| 5,162,563 | 11/1992 | Nishihira et al. | 558/260 |
| 5,315,032 | 5/1994 | Nishihira et al. | 560/157 |

FOREIGN PATENT DOCUMENTS

| | | |
|---|---|---|
| 0065026 | 11/1982 | European Pat. Off. . |
| 982785 | 2/1965 | United Kingdom . |

OTHER PUBLICATIONS

Shiyou Yamazaki, "Preparation of Carbamate Compounds", Japanese Abstract vol. 2, No. 34 (C–77) 1978.

*Primary Examiner*—José G. Dees
*Assistant Examiner*—Barbara S. Frazier
*Attorney, Agent, or Firm*—Finnegan, Henderson, Farabow, Garrett & Dunner

[57] ABSTRACT

Disclosed is a process for preparing carbamates comprising reacting carbonic acid diester with ammonia or amines in a liquid phase in the presence of at least 1 mole % of water based on carbonic acid diester.

13 Claims, No Drawings

PROCESS FOR PREPARING CARBAMATES

This application is a continuation of prior application Ser. No. 077976,669 filed Nov. 16, 1992, now abandoned, which was a continuation of application Ser. No. 07/673,403, filed Mar. 22, 1991, now abandoned.

BACKGROUND OF THE INVENTION

This invention relates to a novel process for preparing carbamates.

Carbamates are a basic organic compound and a useful substance as a material for pharmaceuticals and agricultural chemicals, or as a reagent for qualitative analysis of organic compounds (used as a crystalline derivative for confirmation of alcohols or phenols). Particularly, its ethyl ester is also called "urethane" and has various uses as a raw material of a sleeping drug.

As a process for preparing carbamates, a process of heating alcohol with urea has been known as a conventional technique. For example, in U.K. Patent No. 982,785, there has been disclosed a process in which an aliphatic monohydric alcohol having up to 8 carbon atoms and urea are mixed in a proportion of at least two moles of said alcohol per mole of urea, and the mixture obtained is heated for not more than 1.5 hours in the absence of a catalyst at a temperature in the range of 180° to 230° C. to react said alcohol with urea, during which a venting rate of ammonia gas which is a by-product from the "mixture which is being heated" is controlled to maintain a pressure of the system within the vapor pressure of said "mixture which is being heated". Also, in U.S. Patent No. 3,013,064, there has been disclosed a process for preparing a lower alkyl carbamate by reacting a lower alkanol having 1 to 3 carbon atoms with urea at a temperature of 130° to 155° C. and a pressure of 3 to 10 atmospheres while withdrawing vapor occurred from the reaction zone.

On the other hand, a process of reacting chloroformate with ammonia and a process of reacting alcohol with phosgene and ammonia (literature name: Annalen, vol. 10, p. 284) have been also known as a conventional technique.

As a process for preparing carbamates of which a starting material is carbonic acid diester, as disclosed in Japanese Unexamined Patent Publication No. 503627/1989, there has been known a process in which said carbonic acid diester are reacted with amines in the presence of amidines as a strong organic base catalyst at a temperature of 0° to 100° C. and at a pressure of 1 to 10 bar.

Further, in Japanese Unexamined Patent Publications No. 14745/1977 and No. 163528/1979, there has been disclosed processes in which a hydroxide of an alkali metal or an alkali earth metal or an alcoholate is used as a catalyst.

However, the above process of reacting alcohol with urea requires high temperature or high pressure, whereby installation for manufacture becomes complicated, and the process of reacting chloroformate with ammonia has problems that chloroformate is expensive and a corrosive hydrochloric acid is by-produced. Further, in the process of reacting alcohol with phosgene and ammonia, extremely toxic phosgene should be handled, whereby there is a problem in the point of safety, and also a corrosive hydrochloric acid is by-produced similarly as in the case of the process of reacting chloroformate with ammonia.

The process of using a strong organic base as a catalyst involves problems that the catalyst itself is very expensive and steps for purifying carbamates which are the desired products become complicated. Further, even in the process of using a hydroxide of an alkali metal or an alkali earth metal or an alcoholate as a catalyst, it involves a drawback that steps for purifying carbamates such as separation and removal of a catalyst from a reaction product become complicated.

Accordingly, the processes for preparing carbamates of the prior art are not necessarily industrially satisfied.

The conventional processes for preparing carbamates involve various problems, as described above, that high temperature and high pressure are required for reaction, a corrosive hydrochloric acid is by-produced and steps for purifying carbamates are complicated.

SUMMARY OF THE INVENTION

Accordingly, an object of the present invention is to provide a novel process for preparing carbamates by using a commercially available and cheap material with high yield under mild conditions.

The present inventors have studied intensively in order to accomplish a simple and cheap process for preparing carbamates which can cancel various drawbacks in the conventional processes as described above, and consequently found a process for preparing carbamates by using carbonic acid diester as a starting material without using a catalyst, to accomplish the present invention.

That is, the present invention relates to a process for preparing carbamates comprising reacting carbonic acid diester with ammonia or amines in a liquid phase in the presence of at least 1 mole % of water based on a carbonic acid diester without using a catalyst.

DESCRIPTION OF THE PREFERRED EMBODIMENTS

In the following, the process of the present invention is described in more detail.

As the carbonic acid diester which is one of the starting materials in the process of the present invention, carbonic acid diesters having the same ester groups as that of the desired carbamates are used. As a kind of the ester group which can be used, there may be mentioned, for example, straight or branched saturated hydrocarbon groups having 1 to 8 carbon atoms such as methyl, ethyl, n-propyl, isopropyl, n-butyl, isobutyl, t-butyl and hexyl, alicyclic hydrocarbon groups having 5 to 10 carbon atoms such as cyclohexyl and cyclododecyl, and aromatic hydrocarbon groups having 6 to 12 carbon atoms such as phenyl and benzyl. The process for preparing the carbonic acid diester is not particularly limited, but as a preferred process, there may be mentioned a process previously proposed by the present inventors in Japanese Patent Application No. 274816/1989 which corresponds to our co-pending U.S. Ser. No. 07/599,134 and European Patent Application No. 90 311 469.2.

As amines which are the other starting material, there may be mentioned, in addition to ammonia, straight or branched aliphatic primary and secondary amines having 1 to 12 carbon atoms such as methylamine, ethylamine, n-propylamine amine, isopropylamine, n-butylamine and isobutylamine, aromatic amines such as aniline, benzylamine and o-toluidine, and alicyclic amines such as cyclopropylamine, cyclobutylamine and cyclohexylamine, and further, a commercially available aqueous solution thereof, for example, a 50% aqueous solution of dimethylamine or a 70% aqueous solution of monoethylamine can be used without any problem.

Next, in the process of the present invention, the reaction of said carbonic acid diester with ammonia or said amines can be effected under extremely mild conditions.

For example, the reaction pressure is not particularly limited, and it may be either normal pressure or under pressure. Practically, the reaction can be carried out preferably at a pressure in the range of normal pressure to 100 kg/cm² G.

Further, the reaction can be effected under mild conditions of a reaction temperature in the range of 5° to 200° C., preferably 10° to 120° C.

In the reaction of the carbonic acid diester with ammonia or the amines, a solvent is not necessarily required, but it may be added without any problem for the purpose of improving workability. In this case, a kind of the solvent which can be used suitably is not particularly limited as far as it is inert to water, carbonic acid diester, ammonia or amines which are starting materials, and carbamates which are the desired products, and there may be preferably included, for example, alcohols such as methanol, ethanol, n-propanol, isopropanol, n-butanol and isobutanol, aromatic hydrocarbons such as benzene, toluene and xylene, aliphatic or alicyclic hydrocarbons such as n-hexane, n-heptane and cyclohexane, ethers such as diisopropyl ether, tetrahydrofuran and ethylene glycol dimethyl ether, and nitriles such as acetonitrile, propionitrile and benzonitrile, and further, dimethylformamide and dimethylsulfoxide can be also used. However, in consideration of economy and solubility of the desired carbamates in these solvents, the above alcohol type solvents and hydrocarbon type solvents are particularly preferably used. More preferably, water can be used as a solvent, but when there is no practical merit brought about thereby, it is not required to be added.

The amount of these inert solvents to be used is not particularly limited as far as it is not less than the amount by which the desired carbamates can be dissolved. However, as described below, in consideration of the points that it is necessary to recover these solvents from a reaction mixture, that consumption energy therefor should be lowered as far as possible and that commercial production should be made possible, the amount of these solvents to be used should be minimized, and may be generally 1 to 20 parts by weight, preferably 1 to 3 parts by weight per 1 part by weight of the carbonic acid diester.

In the process of the present invention, a charging ratio of the respective starting materials to be used in the above reaction is described below. As a matter of course, these values are not particularly limited, but should be practical values.

The amount of water to be added is related to the reaction temperature and reaction pressure. The amount may be 1 mole % or more, preferably 10 mole % or more, more preferably 20 mole % or more based on the carbonic acid diester which is a starting material, and yet it may be preferably 0.5% by weight or more, more preferably 2% by weight or more, most preferably 4% by weight or more in the whole reaction system. Incidentally, its upper limit is not particularly limited, but it should be so determined that commercial production is made possible, and may be 30-fold mole or less, preferably 10-fold mole or less based on the carbonic acid diester. Particularly, in the process for preparing carbamates by reacting carbonic acid diester with ammonia, which is a preferred embodiment of the present invention, for forming a uniform liquid phase reaction system, the amount of water to be added may be 10 mole % to 30-fold mole, preferably 20 mole % to 10-fold mole based on the carbonic acid diester. Specifically, the reaction rate of the carbonic acid diester with ammonia or the amines becomes slower as the concentration of water is lowered. The reaction rate can be recovered by raising the reaction temperature slightly, but when the concentration of water is too low, extremely high temperature is required, and accompanying with it, amounts of by-products such as urea are also increased. On the other hand, when the concentration of water becomes high, the reaction rate of the carbonic acid diester with ammonia or the amines is sufficient even at low temperature, but even when 10-fold mole or more of water is added, the above reaction rate will not be further increased, and also when the concentration of water becomes too high, the concentration of carbamates formed is lowered, which results in a problem in productivity such as steps for separation and purification. Thus, practically, for maintaining the rate of the reaction of the carbonic acid diester with ammonia or the amines, the amount of water to be added and the reaction temperature are preferably controlled appropriately within the range as described above.

The amount of ammonia or the amines to be used is also related to the reaction temperature and reaction pressure. However, the charging ratio may be equimolar or more based on the carbonic acid diester, and as an extreme example, it is also possible to use ammonia or the amines as a solvent. However, when the excessive amount of ammonia or the amines becomes smaller, the reaction rate of the carbonic acid diester with ammonia or the amines becomes slower, and therefore the amount may be preferably 1.2-fold mole or more. Also in this case, since it is possible to use ammonia or the amines as a solvent, its upper limit is not particularly required to be determined. However, in consideration of the point of making commercial production possible, the amount of ammonia or the amines to be used may be 1 to 20-fold mole, preferably 1.2 to 10-fold mole, more preferably 2 to 5-fold mole based on the carbonic acid diester.

In the liquid phase reaction of the carbonic acid diester with ammonia or the amines in the process of the present invention, special instruments are not required. The instrument for reaction may be a general stirring tank. Further, a material of this stirring tank may be those generally used in instruments for a reaction system in which ammonia or the amines described above are used.

The reaction of the carbonic acid diester with ammonia or the amines is desirably carried outby supplying the above stirring tank with the predetermined amounts of the carbonic acid diester and ammonia or the amines which are starting materials, and water, respectively, and an inert solvent, if necessary, and stirring the mixture. The stirring rate is not particularly limited, but in general, it may be preferably 300 to 400 rpm. Particularly, when a solvent having no mutual solubility to water is used, vigorous stirring is preferred.

In the case when the reaction of the carbonic acid diester with ammonia or the amines is effected in the presence of the inert solvent as described above, after completion of the reaction, excessive ammonia or the amines and the solvent are recovered from the reaction mixture by, for example, distillation and separation, and thereafter, by selecting suitably a conventional operation such as distillation or crystallization, the desired carbamates can be easily isolated and purified.

EXAMPLES

The process of the present invention is described below in detail by referring to Examples and Comparative example, but the present invention is not limited to these Examples.

Example 1

In a three-necked flask having an inner volume of one liter and equipped with a stirring device, a reflux condenser and a thermometer, 180 g (2 mole) of dimethyl carbonate was charged, and 364 g of 28% by weight of aqueous ammonia (ammonia: 6 mole, water: 14.6 mole) was added dropwise thereto over 30 minutes while stirring. After completion of the above dropwise addition of the aqueous ammonia, stirring was further continued at a temperature in the range of 25° to 30° C. for 4 hours. The reaction mixture thus obtained was applied to gas chromatography to quantitative analyses of dimethyl carbonate and the desired methyl carbamate. As the result, it was found that the conversion of dimethyl carbonate was 99.2%, and the selectivity to methyl carbamate was substantially 100%.

Example 2

In an autoclave having an inner volume of one liter and equipped with a stirring device, a reflux condenser and a thermometer, 135 g (1.5 mole) of dimethyl carbonate, 400 ml of methanol and 5.4 g (0.3 mole) of distilled water were charged, and the autoclave was tightly closed. Thereafter, 127 g (7.5 mole) of liquid ammonia was injected, and the temperature was elevated up to 80° C. while stirring. After the reaction was continued for 6 hours in this state, quantitative analysis of the reaction mixture obtained was effected by using gas chromatography. It was found that the conversion of dimethyl carbonate which is a starting material was 97.5% and the selectivity to the desired methyl carbamate was 98.3%.

Example 3

The reaction of dimethyl carbonate with ammonia was carried out in the same manner as in Example 2 except for charging 400 ml of acetonitrile in place of methanol. The quantitative analysis of the reaction mixture obtained was effected by using gas chromatography. As the result, it was found that the conversion of dimethyl carbonate was 98.1%. Further, it was also found that the selectivity to the desired methyl carbamate was 98.5%.

Comparative Example 1

The reaction of dimethyl carbonate with ammonia was carried out in the same manner as in Example 2 except for not charging 5.4 g of distilled water and changing the reaction Lime from 6 hours to 10 hours. The quantitative analysis of the reaction mixture obtained was effected by using gas chromatography. As the result, it was found that the conversion of dimethyl carbonate was 2.7% and the selectivity to the desired methyl carbamate was substantially 100%.

Example 4

In a three-necked flask having an inner volume of one liter and equipped with a stirring device, a reflux condenser and a thermometer, 180 g (2 mole) of dimethyl carbonate was charged, and 270 g of 50% by weight of an aqueous dimethylamine solution (dimethylamine: 3 mole, water: 7.5 mole) was added dropwise thereto over 15 minutes while stirring. After completion of the dropwise addition, stirring was further continued at a temperature of 25° to 30° C. for 2 hours. The reaction mixture thus obtained was applied to gas chromatography to effect quantitative analysis. As the result, it was found that the conversion of dimethyl carbonate was 99.5%, and the selectivity to methyl N-dimethylcarbamate was substantially 100%.

Example 5

In a three-necked flask having an inner volume of one liter and equipped with a stirring device, a reflux condenser and a thermometer, 180 g (2 mole) of dimethyl carbonate was charged, and 360 g of 50% by weight of an aqueous ethylamine solution (ethylamine: 4 mole, water: 10 mole) was added dropwise thereto over 15 minutes while stirring. After completion of the dropwise addition, stirring was further continued at a temperature of 25° to 30° C. for 3 hours. The reaction mixture thus obtained was applied to gas chromatography to effect quantitative analysis. As the result, it was found that the conversion of dimethyl carbonate was 98.9%, and the selectivity to methyl N-ethylcarbamate was substantially 100%.

As described above, the conventionally known processes for preparing carbamates are not necessarily satisfied as an industrial process because high temperature or high pressure is required, a corrosive hydrochloric acid is by-produced or steps for purifying carbamates are complicated. To the contrary, the process of the present invention has effects which can provide the above novel process for preparing carbamates using a commercially available and cheap starting material, by which carbamates can be prepared with high yield under mild conditions by extremely easy operations,

We claim:

1. A process for preparing a carbamate comprising reacting a carbonic acid diester selected from the group consisting of at least one of dimethyl carbonate diethyl carbonate, di-n-propyl carbonate, diisopropyl carbonate, di-n-butyl carbonate, diisobutyl carbonate, di-t-butyl carbonate, dihexyl carbonate, dicyclohexyl carbonate and dicyclododecyl carbonate with ammonia in the liquid phase in the presence of at least 1 mole % of water based on said carbonic acid diester and without a catalyst.

2. The process according to claim 1, wherein the reaction is carried out at a normal pressure to 100 kg/cm$^2$G.

3. The process according to claim 1, wherein the reaction is carried out at a temperature of 5° to 200° C.

4. The process according to claim 3, wherein the reaction is carried out at a temperature of 10° to 120° C.

5. The process according to claim 1, wherein an amount of water is 10 mole % to 30-fold mole based on the carbonic acid diester.

6. The process according to claim 1, wherein an amount of ammonia is 1 to 20-fold mole based on carbonic acid ester.

7. The process according to claim 6, wherein an amount of ammonia is 1.2 to 10-fold mole.

8. The process according to claim 7, wherein an amount of ammonia is 2 to 5-fold mole.

9. The process according to claim 1, wherein the reaction is carried out in the presence of a solvent selected from the group consisting of an alcohol an aromatic hydrocarbon, an aliphatic or alicyclic hydrocarbon, an ether and a nitrile.

10. The process according to claim 1, wherein the reaction is carried out in the presence of a solvent selected from the group consisting of methanol, ethanol, n-propanol, isopropanol, n-butanol, isobutanol, benzene, toluene, xylene, n-hexane, n-heptane, cyclohexane, diisopropyl ether, tetrahydrofuran, ethylene glycol dimethyl ether, acetonitrile, propionitrile, benzonitrile, dimethylformamide and dimethylsulfoxide.

11. The process according to claim 9, wherein the reaction is carried out in the presence of a solvent selected from the group consisting of methanol, ethanol, n-propanol, isopropanol, n-butanol, isobutanol, benzene, toluene, xylene, n-hexane, n-heptane and cyclohexane.

12. A process for preparing carbamates comprising reacting a carbonic acid diester selected from the group consisting of dimethyl carbonate, diethyl carbonate, di-n-propyl carbonate, diisopropyl carbonate, di-n-butyl carbonate, diisobutyl carbonate, di-t-butyl carbonate, dihexyl carbonate, dicyclohexyl carbonate and dicyclododecyl carbonate with ammonia in an amount ranging from about 1 to about 20 moles of ammonia per mole of carbonic acid diester, in a liquid phase in the presence of a solvent, and in the presence of water in an amount ranging from about 0.10 to about 30 moles per mole of carbonic acid diester, and without a catalyst, at a pressure ranging from atmospheric pressure to 100 $kg/cm^2G$ and at a temperature ranging from about 10° to about 120° C.

13. The process according to claim 12, wherein said solvent is selected from the group consisting methanol, ethanol, n-propanol, isopropanol, n-butanol, isobutanol, benzene, toluene, xylene, n-hexane, n-heptane, cyclohexane, diisopropyl ether, tetrahydrofuran, ethylene glycol dimethyl ether, acetonitrile, propionitrile, benzonitrile, dimethylformamide and dimethylsulfoxide.

* * * * *